United States Patent [19]  [11] 3,992,379
Liebenow et al. [45] Nov. 16, 1976

[54] 4-ALKYLDIOXYALKYLENE-5-BENZYLPYRIMIDINES
[75] Inventors: Walter Otto Liebenow, Nurnberg; Jaroslav Prikryl, Erlangen, both of Germany
[73] Assignee: Ludwig Heumann & Co. GmbH, Nurnberg, Germany
[22] Filed: Mar. 15, 1974
[21] Appl. No.: 451,595

[30] Foreign Application Priority Data
Mar. 17, 1973 Germany............................ 2313361

[52] U.S. Cl. ................... 260/256.4 N; 260/251 R; 260/465 F; 260/473 A; 260/473 R; 424/251
[51] Int. Cl.[2] ........................................ C07D 239/48
[58] Field of Search ............................ 260/256.4 N

[56] References Cited
UNITED STATES PATENTS

| | | | |
|---|---|---|---|
| 2,909,522 | 10/1959 | Hitchings et al. | 260/256.4 N |
| 3,670,077 | 6/1972 | Freeman | 260/256.4 N |
| 3,671,564 | 6/1972 | Cresswell et al. | 260/256.4 N |
| 3,692,787 | 9/1972 | Roth et al. | 260/256.4 N |
| 3,772,289 | 11/1973 | Roth et al. | 260/256.4 N |
| 3,819,629 | 6/1974 | Roth et al. | 260/256.4 N |
| 3,849,407 | 11/1974 | Cresswell et al. | 260/256.4 N |

OTHER PUBLICATIONS
Roth et al., Chem. Abst., vol. 70, col. 96812k, (1969).
Roth et al., J. Med. Pharm. Chem., vol. 5, pp. 1103—1123, (1962).

*Primary Examiner*—Nicholas S. Rizzo
*Assistant Examiner*—Mary C. Vaughn
*Attorney, Agent, or Firm*—Frank J. Jordan

[57] ABSTRACT

Bactericidal 4'-alkyldioxyalkylene-5-benzylpyrimidines, process for their production, and pharmaceutical compositions or formulations thereof, containing compounds of the general formula:

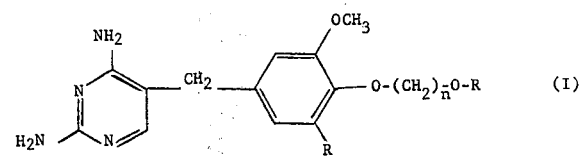

wherein $R_1$ is an alkyl group containing from 1 to 3 carbon atoms, R is an atom of hydrogen, an atom of halogen, or an alkyl or alkoxy group containing from 1 to 3 carbon atoms, and $n$ is an integer of from 1 to 3, exhibit excellent bactericidal activity and low toxicity and are suitable for oral administration.

3 Claims, No Drawings

4-ALKYLDIOXYALKYLENE-5-BENZYLPYRIMIDINES

BACKGROUND OF THE INVENTION

The present invention relates to bactericidal 4'-alkyl-dioxyalkylene-5-benzyl pyrimidines having the following general Formula I:

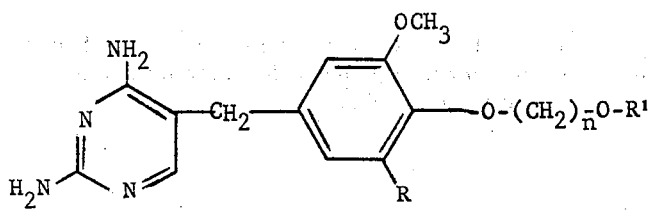

and the pharmaceutically acceptable acid addition salts thereof, wherein $R_1$ is an alkyl group containing from 1 to 4 carbon atoms, R is an atom of hydrogen, an atom of halogen, or an alkyl or alkoxy group containing from 1 to 3 carbon atoms, and $n$ is an integer of from 1 to 3. Of these, the 2, 4diamino-5-(4'alkyldioxyalkylene-benzyl)-pyrimidines having the following Formula II are preferred compounds.

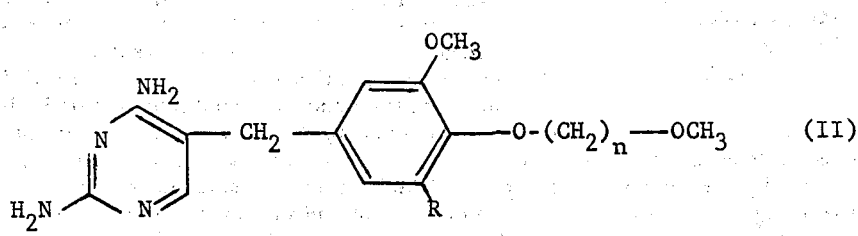

wherein R denotes an atom of hydrogen, an atom of halogen, an alkyl or methoxy group, and $n$ is an integer of 1 or 2.

Suitable representative pharmaceutically acceptable acid addition salts of the foregoing compounds of Formulas I and II are those, for example, derived from hydrochloric acid, phosphoric acid, sulphuric acid, lactic acid, citric acid, tartaric acid, fumaric acid, maleic acid, ascorbic acid, etc.

DESCRIPTION OF THE PRIOR ART

It has been heretofore disclosed in the literature that 2,4-diamino-5- (3'-4'-dimethoxybenzyl)-pyrimidine has bactericidal activity and that such activity is present in the maximum degree in the compound 2,4-diamino-5-(3'-4'-5'-trimethoxybenzyl)-pyrimidine. All modifications of the cyclic aromatic compound, however, have resulted in less effective compounds (see J. Med. Pharm. Chem. 5, p. 1118, Tab. 9).

It has now been discovered, surprisingly, in the present invention that novel compounds such as 2,4-diamino-5-(3',5'-dialkoxy-4'-alkyl-dioxyalkylene-benzyl)-pyrimidines have an excellent anti-bacterial action and the advantage, moreover, of a substantially higher degree of solubility in water and in lipins (lipids, lipoids) compared to the known 2,4-diamino-5-(3',4',5'-trimethoxy-benzyl)-pyrimidine. These physical properties are required in order to meet the fundamental needs for resorption required in oral adminstration.

The novel, bactericidally active compounds of this invention, i.e., the 2,4-diamino-5-(3',5'-dimethoxy-4'-methyldioxy-ethylenebenzyl)-pyrimidines are especially characterized by having a substantially lower degree of toxicity coupled with an improved anti-bacterial action, compared with the conventional bactericide 5-nitro-8-hydroxycholine that is known in the literature and used in practice as a chemotherapeutic, in combination with sulphonamide.

SUMMARY OF THE INVENTION

As previously noted, this invention relates generally to bactericidal 4'-alkyldioxyalkylene-5-benzylpyrimidines of the formula:

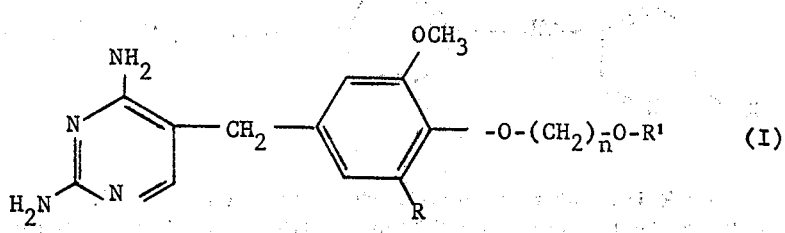

In another aspect of this invention, there is also provided a process for the production of the foregoing 2,4-diamino-5-(3',5'-disubstituted-4'-alkyldioxy-alkylene-benzyl)-pyrimidine of Formula I.

DESCRIPTION OF THE PREFERRED EMBODIMENTS

The above novel process is characterized by (1) formulating a hydrocinnamic acid ester of the general Formula III below:

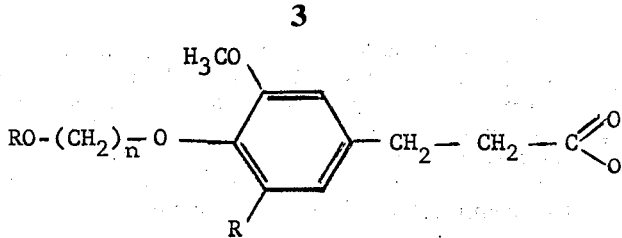

wherein R, R¹, and n are the same as in Formula I, the formulation being effected with formic acid ester in the presence of sodium and (2) condensing the formulation with guanidine in an alkaline medium. The 2-amino-4-hydroxy-5-benzyl-substituted pyrimidine obtained thereby is further reacted with phosphoroxychloride and the resultant chlorine compound is then reacted with ammonia to form the desired end products.

Alternatively the production of the present compounds of Formula I comprises reacting appropriately alkylsubstituted formyl-hydrocinnamic acid nitriles having the Formula IV:

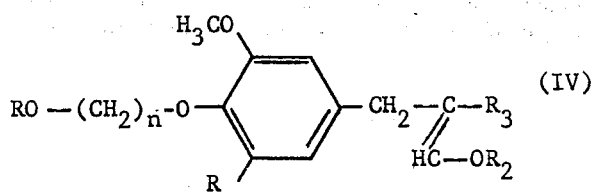

wherein $R_1$ and $R_2$ are an alkyl group, R an atom of hydrogen, an atom of halogen, an alkyl or alkoxy group, and $R_3$ a carbalkoxy or nitrile group, with guanidine in an alkaline medium to form compounds having the Formula I.

Another alternative for the production of compounds of Formula I consists in reacting, under pressure, a 2-methylmercapto-4-chloro-5-benzyl-pyrimidine or a 2-methylsulphonyl-4-chloro-5-benzyl-substituted pyrimidine having the Formula V:

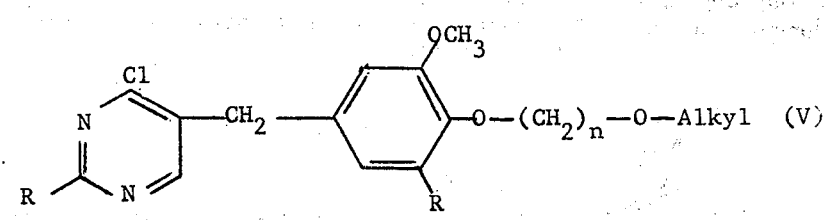

wherein $R_4$ is an alkylmercapto or alkylsulphonyl group in which the alkyl group is preferably a methyl group, with alcoholic ammonia. The compounds in accordance with the invention may also be produced by reacting compounds having the general Formula VI:

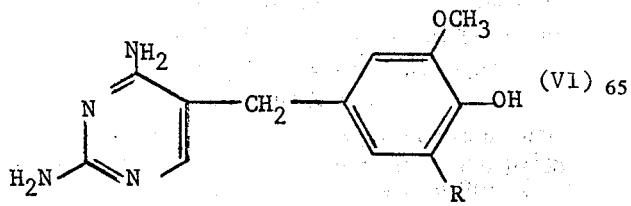

wherein R is an atom of hydrogen, an atom of halogen, an alkyl or alkoxy group, with an alkylating agent of the Formula VII:

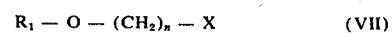

$$R_1 - O - (CH_2)_n - X \qquad (VII)$$

wherein X is a conventional reactive atom or a reactive group. The alkylation of the 4-OH group may be performed by reaction with an alkoxy-alkyl halide or with an alkoxy-alkyl-p-toluenesulfonic acid ester in a polar solvent such as ethanol, methoxy-ethanol or dimethylsulphoxide in the presence of a base such as sodium ethoxide or potassium hydroxide.

All of the foregoing compounds having the respective Formulae I, II, III, IV, V and VI are new compounds and are included in the scope of this invention.

In another aspect of this invention, there is provided a pharmaceutical composition applicable for oral administration containing the conventional carrier substances customarily used and, as active ingredient, a compound of the Formula I either alone or in combination with other active substances, e.g. sulphonamides. Suitable carrier substances for oral administration of dry forms of the present pharmaceutical composition, e.g. tablets, capsules, etc., include aerosil, cellulose, dextrose, corn starch, sucrose, talcum, magnesium stearate, calcium hydrophosphate, lactose, gelatine, polyvinylpyrrolidone, etc. Suitable additives for use when administrating the present pharmaceutical compositions in liquid form include, for example, solutions or suspensions of carboxymethylcellulose, cellulose, sorbitol, sucrose, sugar colouring and of flavouring substances in water.

In addition, the compounds of Formula I can be administered in the form of aqueous solutions for injection, e.g. in buffered solution, and as such are suitably introduced into the host by parenteral administration.

By way of comparison to the most powerful antibacterial compound, i.e. the known 2,4-diamono-5-(3',4',-5',-trimethoxybenzyl)pyrimidine, previously discussed above, which has solubility of 67 mg in 100 ml of water over a longer period, it is to be noted that the 2,4- diamino-5-(3',5'-dimethoxy-4'-methyldioxy-ethylenebenzyl)-pyrimidine compound of this invention for example, is soluble at the rate of 800 mg in 100 ml of water. Thus, it can be readily seen that this improvement in solubility is of special importance, particularly if the administration of such a solution intended for injection is added, in combination, with another or other active ingredient, as for example, sulphonamides. An improvement in the active antibacterial substance can be obtained by combining compounds of Formula I (the preferred compound among these, as noted, being 2,4-diamino-5-(3'5',-dimethoxy-4'-methyldioxyethylene-benzyl)-pyrimidine), with sulphonamides, e.g. with sulphadiazine, sulphdiamidine, sulphamethoxazol, sulphamerazine, sulphamethoxydiazine and sulpha-dimethoxine, etc. Tablets or other solid dosage forms containing the active substance of Formula I either alone or in combination with the sulphonamides are examples of suitable form of administration of such combinations of active ingredients. The effective dosage for humans of the present pharmaceutical compositions is between 20 to 1000 mg/day, preferably 100 to 200 mg/day.

The present invention is further illustrated by the following non-limiting examples.

EXAMPLE 1

Production of 2,4-diamino-5-(3',5'-dimethoxy-4'-methyldioxyethylene-benzyl)-pyrimidine.

a. 50 ml of toluol and 16 ml of sodium methylate were placed in a 1-liter flask having a flat-ground base and equipped with an "anchor" stirrer and cooled to 10° C. 62 g of 3,5-dimethoxy-4-methyldioxyethylene-hydrocinnamic acid ethyl ester and 14.0 g of formic acid ethyl ester were added dropwise at approx. 12° C, under vigorous agitation. Stirring was then continued for 4 hours and the flask was allowed to stand overnight. The viscous reactive mixture had added thereto 19 g of guanidine hydrochloride, 10.7 g of sodium methylate and 200 ml of methanol, and was heated for 2 hours under reflux conditions. The solvents were distilled off and the residue was dissolved in water. The aqueous solution was adjusted to pH 5 by means of glacial acetic acid and the precipitated 2-amino-4-hydroxy-5-(3'5'-dimethoxy-4'-methyldioxyethylene-benzyl)-pyrimidine was drawn off and dried at room temperature.

b. 28 ml of phosphoroxychloride was placed in a 1-liter flask and 33 g of the 2-amino-4-hydroxy-pyrimidine compound described above was added thereto. A thick mash was formed, which liquefied under heating action. During the cooling operation, to the reactive solution was added an admixture of a mixture of ice and water, and the pH value of the resulting solution was maintained at pH 7 to 8 by addition of ammonia. This mixture was allowed to stand for 1 to 2 days, and the solid precipitate was then drawn off. The 2-amino-4-chloro-5'-(3'-5'-dimethoxy-4'-methyldioxy-ethylene-benzyl)-pyrimidine was dried at 120° C until its weight was constant, and was brought into use again.

c. 800 ml of an alcoholic solution containing 150g of ammonia was placed in an autoclave, and 177g was added of well-ground 2-amino-4-chloro-pyrimidine derivative. This mixture was heated to 160° C. After cooling, the suspension was drawn off, washed with a little ethanol and recrystallized in water. The melting point was between 152° and 155° C.

| Analysis: | calculated for $C_{16}H_{22}N_4O_4$ | determined: |
|---|---|---|
| | C = 57.47 | C = 56.95 |
| | H = 6.63 | H = 6.43 |
| | N = 16.76 | N = 16.79 |
| | O = 19.14 | O = 19.83 |

EXAMPLE 2

Production of 2,4-diamino-5-(3'-5'-dimethoxy-4'-methyldioxymethyl-benzyl)-pyrimidine.

225 g of 3,5-dimethoxy-4-methyldioxymethylene-benzaldehyde and 125 g of β-methoxypropionitrile were stirred into a paste and mixed with 700 ml of sodium methylate (containing 70g of sodium) at 5° to 10° C. After stirring overnight, 59 g was added of guanidine base dissolved in 500 ml of methanol, and the whole was heated for 20 hours under reflux conditions. The precipitated product was drawn off and the reactive solution was concentrated further. The total precipitated product was dissolved in water and filtered through activated charcoal.

The melting point of the precipitated product was 185° C.

| Analysis: | calculated for $C_{15}H_{20}N_4O_4$ | determined: |
|---|---|---|
| | C = 56.25 | C = 56.77 |
| | H = 6.29 | H = 6.62 |
| | N = 17.49 | N = 17.42 |
| | O = 19.98 | O = 20.15 |

EXAMPLE 3

Production of 2,4-diamino-5-(3',5'-dimethoxy-4'-methyldioxyethylene-benzyl)-pyrimidine.

1.5 g of Na was dissolved in 100 ml of 2-methoxyethanol, and 15.5 g of 2,4-diamino-5-(3'-5'-dimethoxy-4'-hydroxybenzyl)-pyrimidine and 14.2 g of p-toluenesulphonic acid-(2'-methoxy)ethyl ester were added thereto. Heating was performed for 3 hours under reflux conditions and the sodium p-toluenesulphonate was then drawn off. The 2-methoxyethanol was then distilled off, and the residue was dissolved in water and shaken up several times with chloroform. After the chloroform had been distilled off, the residue was recrystallized in water.

Melting point of product: 153° to 156° C.

EXAMPLE 4

Production of 2,4-diamino-5-(3'-methoxy-4'-methyldioxymethylenebenzyl)-pyrimidine.

The synthesis herein was performed analogously to Example 2.

The product required was first recrystallized in water and then in water/methanol =2/1.

Melting point of product: 163° to 165° C.

| Analysis: | calculated for $C_{14}H_{18}N_4O_3$ | determined: |
|---|---|---|
| | C = 57.92 | C = 58.39 |
| | H = 6.25 | H = 6.43 |
| | N = 19.30 | N = 19.96 |
| | O = 16.53 | O = 15.27 |

EXAMPLE 5

Production of a tablet from the following ingredients by direct compression.

50 mg of 2,4-diamino-5-(3'-5'-dimethoxy-4'-methyl-dioxy-ethylenebenzyl)-pyrimidine
250 mg of sulphadiazine
45 mg of "Miamite"
80 mg of microgranular cellulose
30 mg of "Primogel"
15 mg of Mg stearate The tablet thus produced represents a dosage form suitable for administration to humans for treatment of bacterial infections.

EXAMPLE 6

In this example, the superior therapeutic action of the present preferred active ingredient and its low toxicity were demonstrated by the following comparative data:

| $LD_{50}$ in the case of rats: | |
|---|---|
| 5-nitro-8-hydrocholine (substance A) | 830 mg/kg |
| 2,4-diamino-5-(3',5'-dimethoxy-4'-methyldioxy-ethylene-benzyl)-pyrimidine (substance B) | 1357 mg/kg |

The test for anti-bacterial action in vivo was performed with discs which were each impregnated with 25 µg of the two substances A and B:

| Substance | | Arresting Circle Diameter |
|---|---|---|
| substance A | 25 coli strains | $\bar{x} = 20.7$ mms |
| substance B | 25 coli strains | $\bar{x} = 28.5$ mms |

In view of the improved effectiveness and in particular of the substantially lower degree of toxicity, these values demonstrate that the present compound has a greater therapeutic spectrum as compared to the conventional bactericidal substance.

It is thought that the invention and many of its attendant advantages will be understood from the foregoing description and it will be apparent that various changes may be made in the matter of the ingredients, their identity, and their proportions and in the steps of the process and their order or accomplishment without departing from the spirit and scope of the invention or sacrificing all of its material advantages, the form hereinbefore described being merely a preferred embodiment thereof.

What is claimed is:

1. A 2,4-diamino-5-(4'-alkyldioxyalkylene-benzyl)-pyrimidine having the formula

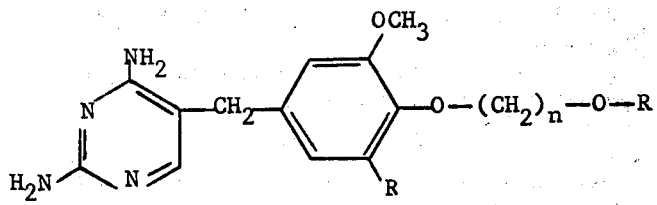

wherein $R_1$ is an alkyl group having from 1 to 3 carbon atoms, R is an alkoxy group having from 1 to 3 carbon atoms, and n is an integer of from 1 to 3, and pharmaceutically acceptable salts thereof.

2. A pyrimidine according to claim 1, said pyrimidine being 2,4-diamino-5-(3',5'-dimethoxy-4'-methyldioxy-ethylenebenzyl)-pyrimidine and the pharmaceutically acceptable salts thereof.

3. A pyrimidine according to claim 1, said pyrimidine being 2,4-diamino-5-(3'-5'-dimethoxy-4'-methyldioxymethylenebenzyl)-pyrimidine and the pharmaceutically acceptable salts thereof.

* * * * *